United States Patent [19]

Yudelson et al.

[11] Patent Number: 4,552,848

[45] Date of Patent: Nov. 12, 1985

[54] MACROMOLECULE DETERMINATION BY PHYSICAL DEVELOPMENT

[75] Inventors: Joseph S. Yudelson; Thomas M. Johnson, both of Rochester, N.Y.

[73] Assignee: Eastman Kodak Company, Rochester, N.Y.

[21] Appl. No.: 495,216

[22] Filed: May 16, 1983

[51] Int. Cl.$^4$ ............................................. G01N 33/68
[52] U.S. Cl. ........................................ 436/86; 436/169
[58] Field of Search ............... 436/86, 87, 169, 903; 430/413, 477, 489

[56] References Cited

U.S. PATENT DOCUMENTS

| | | | |
|---|---|---|---|
| 3,390,998 | 7/1968 | Cole | 430/477 |
| 3,650,748 | 3/1972 | Yudelson et al. | 430/413 |
| 4,144,143 | 3/1979 | Hawkridge et al. | |
| 4,307,168 | 12/1981 | Lelental et al. | 430/414 X |
| 4,434,234 | 2/1984 | Adams et al. | 436/86 |

OTHER PUBLICATIONS

PCT application publication No. WO82/03128, Sep. 16, 1982, by Merril.

*Primary Examiner*—Arnold Turk
*Attorney, Agent, or Firm*—Arthur H. Rosenstein

[57] ABSTRACT

A method for determining macromolecules in polyacrylamide gels comprises forming a latent stain image by nucleating the gel with a palladium tetramine salt and developing the latent stain image by treating the gel with a physical developing solution comprising dimethylamine borane and a member selected from the group consisting of a transition metal salt and a tetrazolium salt.

10 Claims, No Drawings

MACROMOLECULE DETERMINATION BY PHYSICAL DEVELOPMENT

BACKGROUND OF THE INVENTION

1. Field of the Invention

The present invention relates to a method for determining macromolecules such as proteins. The method comprises forming a stain image by nucleating polyacrylamide gels containing the macromolecules with a palladium tetramine salt and developing with a specific physical developer solution.

2. Description of Related Art

The detection of macromolecules such as proteins and polypeptides is extremely important in many areas of biology and clinical medicine such as genetic screening and the diagnosis of genetic diseases. In these areas, the amount of macromolecules that can be detected in cellular extracts of body fluids is determinative.

Electrophoresis is the movement of charged particles in a matrix under the influence of an electrical field. Electrophoresis is the primary laboratory detection and characterization technique for macromolecules (see Chemical and Engineering News 3/14/83, p. 10).

Continuing developments in two-dimensional gel electrophoresis have provided the capability of resolving thousands of macromolecules from complex biological mixtures. However, the inability to detect polypeptides present in low concentration has limited the application of this technology, particularly in clinical screening for pathological states, endocrinology, mammalian metabolism, developmental biology, and immunology.

Because the improved gel electrophoretic techniques greatly increase macromolecule resolution, visual detection methods employing conventional polypeptide dyes are no longer adequate.

The most commonly used conventional macromolecule stain is Coomassie Blue, which may be considered as a prototype. Dyes of this type are mainly dependent upon the electrostatic attraction between dye and polypeptide, stabilized by van der Waals forces. In fact, Coomassie Blue and a variety of other dyes exhibit particular affinities for macromolecules of specific charge. Coomassie Blue, an acidic dye, stains basic macromolecules most intensely, while crystal violet is the most effective stain for acidic macromolecules. Other dyes for which quantitative aspects of staining have been investigated include Amido Black, Fast Green, and $Fe^{2+}$-bathophenanthroline sulfonate. In contrast, the Remazol Brilliant Blue R method depends on a covalent bond between dye and polypeptide. With Coomassie Blue, the minimum amount of a protein that can be detected is approximately 0.2 to 0.5 $\mu$g.

An assortment of other techniques also exist. These include densitometric scanning for absorbance at 280 nm, binding of radiolabelled or fluorescent ligands such as concanavalin A to glycoproteins, binding of antisera to polypeptides at the gel surface, and staining of specific polypeptide moieties.

Radioactive detection techniques offer a higher degree of sensitivity than the stains but are often impractical to use. In vivo radiolabelling may alter cellular metabolism and it may be impossible to label certain human macromolecules. In vitro radiolabelling has the disadvantage that it might alter the electrophoretic mobility of macromolecules. Furthermore, radioactive reagents sometimes prove too expensive and long exposure to detect trace macromolecules may result in the problem of "autoradiographic spreading".

The above staining methods, moreover, are difficult to perform, hazardous, time-consuming, and unless the macromolecules are heavily labeled, lack the sensitivity to detect proteins present in low or trace concentrations. A problem arises, for example, with body fluids, such as cerebrospinal and amniotic fluids, which are often difficult to obtain in quantity and frequently contain certain abundant proteins which cause distortion of electrophoretic patterns when sufficient sample is analyzed to observe specific trace polypeptides.

Another method of visualization involves the use of silver stains. In this method, a swollen polyacrylamide electrophoretic sheet is treated with a silver salt and subsequently developed in a dilute reducing solution such as formaldehyde. An improvement in sensitization is obtained as compared with dye staining. This method entails several washing steps and many of the solutions used are unstable and must be mixed immediately before use. The silver stain method is described in PCT application publication No. WO 82/03128, Sept. 16, 1982 by Merril.

There is a need for a macromolecule visualization procedure that achieves a higher detection sensitivity than obtained with dye staining, and which is similar and more expedient to carry out than is the case with dye and silver staining, or autoradiography.

SUMMARY OF THE INVENTION

This invention provides an improved method for visualizing macromolecules in polyacrylamide gels, said method comprising the steps of (a) forming a latent stain image by nucleating the macromolecules in the gel with a palladium tetramine salt and (b) developing the latent stain image by treating the gel with a physical developer solution comprising dimethylamine borane and a member selected from the group consisting of a transition metal salt and a tetrazolium salt. This method is capable of detecting less than 0.01 mg of macromolecules.

An electrophoregram that consists of a polyacrylamide slab is visualized by nucleation with a palladium tetramine salt and developed in a physical developer comprising a transition metal salt or a tetrazolium salt, dimethylamine borane and optionally an antifoggant.

This method is carried out in a short time as compared to that of the dye and silver stain and autoradiographic methods. While a mixture of a silver salt and a reducing agent is extremely unstable (black reduced silver begins to appear immediately after the two components are in contact), the metal or tetrazolium salt and dimethylamine borane can be mixed and left for days without any sign of reduced metal or dye. Further, sodium dodecyl sulfate (SDS) which is present in the gel matrix, does not interfere with the staining procedure. This is in contrast with silver stains which require careful removal of SDS before the gel is imbibed with a silver salt solution.

Kits comprising solutions of the components used in the method are also described. Use of these kits can find utility in clinical and laboratory examination of blood devices and other macromolecules separated by electrophoresis, diagnosis of metal abnormalities by examination of amniotic fluid, diagnosis of central nervous system disease by analysis of macromolecule patterns in spiral fluid and other applications in which the detection and/or quantitation of macromolecules is desired.

DESCRIPTION OF THE PREFEERRED EMBODIMENTS

The macromolecules to be detected in this invention are preferably proteins, although other macromolecules such as nucleic acids and polypeptides can be detected by the present method.

The electrophoretic separation using polyacrylamide gel slabs is carried out using any of the procedures well known in the art. After the sample believed to contain macromolecules has been introduced into the gel in a conventional manner, the macromolecules are fixed in the gel by treatment with a solution of methanol and water (1:1) for a short period of time. If a fixing agent such as acetic or trichloroacetic acid is used in the fixing step, it is removed by soaking in methanol-water or ethanol-water. The most preferred fixing agent solution is an aqueous mixture of ethanol and/or methanol (about 10–50%). The above fixing agents have been employed in both histology and protein electrophoresis for years. Generally, the gels are fixed by immersion in the fixing agent solution for a period of about 30–60 minutes.

The first steps in this method are generalized preparation of the protein solution, preparation of the gel slabs and loading and running the gels. This process, prior to visualization, is known in the art as the Laemmli System (U. K. Laemmli, Nature, 227, 680–685 (1970)).

Macromolecule solutions are prepared by mixing the macromolecule solution which can contain salts, with an equal volume of a treatment solution consisting of a buffer such as tris (hydrogen methyl) aminomethane hydrochloride (TRIS.HCl), sodium dodecyl sulfate, glycerol and 2-mercaptoethanol.

The mixture is placed in a test tube and immersed into a boiling water bath for 1.5–3 minutes and then chilled in ice. Generally, 1 microliter of this solution contains 0.5 μg of protein. The protein solution is divided into 1 mL lots and stored at −20° C.

The gel slabs are prepared using the Laemmli system described above. It involves 2 gel layers. The layer in which the proteins are separated is referenced to as the "running" layer (separating layer) and the layer in which the protein solutions are applied is referenced to as the "stacking" layer. The stacking layer is discarded prior to the visualization step. The stacking layer allows the protein solution to be concentrated at the top of the separating gel in a narrow band to obtain sharper bands. The gel slabs can be made using the following Stock Solutions:

| | | |
|---|---|---|
| 1. | Monomer Solution | |
| | Acrylamide (electrophoresis grade) | 29.2% (aq) |
| | Methylene bisacrylamide | 0.8% |
| 2. | Running Gel Buffer | |
| | Tris (tris(hydroxymethyl)-aminomethane), free base adjusted to pH 8.8 with HCl | 18.2% |
| 3. | Stacking Gel Buffer | |
| | Tris HCl salt, adjusted to pH 6.8 with HCl | 6.0% |
| 4. | Sodium Dodecyl Sulfate (SDS) | |
| | SDS | 10% |
| 5. | Initiator | |
| | Ammonium peroxydisulfate | 10% |
| 6. | Running Gel Overlay | |
| | Tris (Solution 2) | 18.2% |
| | SDS, adjusted to pH 8.8 | 0.1% |
| 7. | Tank Buffer | |
| | Tris | 0.4% |
| | SDS, adjusted to pH 8.3 | 0.1% |
| 8. | Stain | |
| | Coomassie Blue R-250 | 0.125% |
| | Methanol | 50% |
| | Acetic Acid | 10% |
| 9. | DeStaining Solution I | |
| | Methanol | 50% |
| | Acetic Acid | 10% |
| 10. | DeStaining Solution II | |
| | Methanol | 5% |
| | Acetic Acid | 7% |

The separating gel and the stacking gel solutions are as follows:

| | | |
|---|---|---|
| 11. | Separating Gel | |
| | Monomer Solution | 20 ml |
| | Running Gel Buffer | 15 |
| | SDS | 0.6 |
| | Water | 24.1 |
| | Initiator | 0.3 |
| | Tetramethylethylenediamine (TEMED) | 0.02 |
| 12. | Stacking Gel | |
| | Monomer Solution | 5.4 ml |
| | Stacking Gel Buffer | 10.0 |
| | SDS | 0.4 |
| | Water | 24.4 |
| | Initiator | 0.2 |
| | TEMED | 0.02 |

The separating gel is prepared using a Hoefer Scientific Instruments SE600 Vertical Slab Gel Unit. Different thicknesses (0.75, 1.5 mm) of gel are obtained by the use of plastic spacers.

The separating gel solution without the initiator and TEMED is degassed for approximately 5–10 minutes using a water aspirator. The initiator and TEMED are then added and the solution poured between glass plates (14×16 cm) (using a disposable Pasteur pipet) to a level about 4 cm from the top of the plates. A water layer is then applied above the solution by means of a glass syringe. The solution polymerizes within 15 minutes after which the water layer is discarded and the gel is covered with a few mL of the Running Gel Overlay solution and left overnight.

The stacking gel is prepared as follows: The next day, the gel is rinsed and the stacking gel solution minus the Initiator and TEMED is degassed, after which the polymerization catalysts are added, and the mixture poured over the gel. A plastic comb is inserted in order to mold the sample wells in the gel and the gel is allowed to polymerize for approximately 1 hour. After this time, the comb is removed, the wells formed by the comb are rinsed with water and are then ready for loading.

Loading and running the gels is accomplished as follows: Each well is filled with Tank Buffer and the protein sample is underlayered into each well by means of a 10 μL glass syringe. The glass sandwiches are then placed into the electrophoresis tank which is filled with tank buffer. The upper chamber is filled with this same buffer and the separation is carried out at a current level of 15–30 ma per gel. The voltage varies during a run from an initial value of 85 V to approximately 330 V at the end of the separation (for 2 gels). A tracking dye, bromophenol blue or phenol red, is added to one of the slots at the start. During the separation, the dye migrates with greater velocity than any of the protein fractions. The run is terminated when the dye is within 1–3 cm of the bottom of the glass sandwich.

The visualization steps include the following: The plates are separated, the stacking gel discarded, and the separating gel slab placed into a 300 ml methanol-water (1:1) mixture for washing on a rocking table. After washing for 1 hour, the gels are ready for visualization. For dye visualization, no wash step is required. The gel strip is put into the Stain bath for 4–16 hours. It is then washed in DeStaining Solution I for 2 hours, and then washed in DeStaining Solution II for several hours. This step is generally carried out overnight in order to completely remove the dye from the background areas.

The first step in the visualization method of the present invention comprises treating the fixed electrophotogram with a catalytic metal precursor to form a latent stain image. The catalyst generally used is a palladium tetramine salt such as palladium tetramine chloride or palladium tetramine nitrate. These particular catalysts unexpectedly yield excellent results in that they possess the proper combination of stability and solubility to sensitize the electrophoregram from the macromolecular area. Similar catalysts such as Palladium bis(ethylene diamine) chloride or potassium palladium tetrathiocyanate yield a much lower degree of nucleation (sensitivity), and potassium palladium tetrachloride is too easily reduced to catalytic palladium to give proper image differentiation. In some instances, the SDS presensitizers and the palladium tetramine salt can be combined in one solution. The catalyst is generally present in coverages of from about 0.009 to 1.9 mg/m$^2$.

The development of the latent stain image is accomplished by treating the gel with a developer solution comprising dimethylamine borane as the reducing agent. Other reducing agents result in high fog because they do not adequately differentiate between the image (protein) area and the background.

The developing solution also comprises a transition metal salt or tetrazolium salt physical developer. The tetrazolium salt can be present in the amounts between about 1 mg/0.093 m$^2$ and about 100 mg/0.093 m$^2$ and the reducing agent can be present in amounts between about 1 mg/0.093 m$^2$ and about 200 mg/0.093 m$^2$.

An extremely wide variety of tetrazolium salts may be used in the practice of the present invention. It is understood that the term "tetrazolium salt" throughout the application includes tetrazolium salts, ditetrazolium salts and tetrazolium betaines, and other reducible dye precursors.

Useful tetrazolium salts are described in "The Chemistry of Formazans and Tetrazolium Salts", A. W. Nineham, Chem. Rev., 55, 355 (1955) hereby incorporated by reference. The synthesis of tetrazolium salts and the chelation of formazan dyes are also described in the above reference.

Tetrazolium salts useful in the present invention include compounds having the general formula:

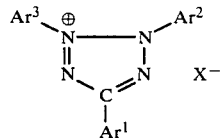

wherein $Ar^1$, $Ar^2$ and $Ar^3$ may be the same or different and represent phenyl groups or phenyl groups substituted with electron withdrawing groups such as nitro, methoxy and the like or electron donating groups such as alkyl; and $Ar^3$ can also represent a 4,5-dialkyl-2-thiazolyl group containing 1 to 5 carbon atoms in the alkyl group or a 2-benzthiazolyl group; and $X^-$ is an anion such as a halide, acetate, tetrafluoroborate and the like.

Specific examples of tetrazolium salts and methods for their preparation can be found in Canadian Pat. No. 860,873, which is hereby incorporated by reference.

Triazolium salts may also be employed as reducible dye precursors in the practice of this invention. These are colorless compounds that are reduced by the process of the invention to colored azo-amine dyes. Exemplary triazolium salts are disclosed in Research Disclosure, Item No. 12617, Vol. 126, October 1974 at Table IV.

Physical developer baths can be made from substantially equal volumes of a solution of a tetrazolium salt and a solution of a reducing agent. The resulting physical developer bath is considered useful if the tetrazolium salt is not spontaneously reduced to formazan dye but is reduced to formazan dye when palladium (0) or other catalyst is added to the bath. By spontaneously, it is meant that the formazan dye is formed essentially instantaneously without the metal nuclei.

The physical developers useful in the present invention can be simple solvent solutions of the tetrazolium salt and the reducing agent. The solvent is one in which the tetrazolium salt is soluble and the corresponding formazan dye as well as the palladium nuclei is insoluble. Mixtures of solvents may also be used to advantage. For example, the solubility of a tetrazolium salt in aqueous solution may be enhanced by the addition of methanol. Other useful solvents besides water include methyl alcohol, ethyl alcohol, acetonitrile and the like.

The solution can be saturated with the tetrazolium salt but is useful with as little as about 0.1% tetrazolium salt by weight of the solvent.

The transition metal salt deposited from the bath must itself be autocatalytic; that is, it must act as a catalyst for further deposition of metal from the developer. This is necessary in order that deposition and development will continue after palladium nuclei are enveloped with heavy metal. With respect to the Periodic Table, suitable heavy metals can be selected from Group VIII metals such as nickel, cobalt, iron, palladium and platinum, Group VIB metals such as chromium and Group IB metals such as copper, silver and gold. Almost any heavy metal salt which is a source of the desired heavy metal ions can be employed. Suitable heavy metal salts useful in the invention include heavy metal halides such as cobaltous bromide, cobaltous chloride, cobaltous iodide, ferrous bromide, ferrous chloride, chromium bromide, chromium chloride, chromium iodide, copper chloride, silver bromide, silver chloride, silver iodide, gold chloride, palladium chloride and platinum chloride, heavy metal sulfates such as nickel sulfate, ferrous sulfate, cobaltous sulfate, chromium sulfate, copper sulfate, palladium sulfate and platinum sulfate, heavy metal nitrates such as nickel nitrate, ferrous nitrate, cobaltous nitrate, chromium nitrate and copper nitrate, and heavy metal salts of organic acids such as ferrous acetate, cobaltous acetate, chromium acetate and copper formate. Baths can be formulated based on a single heavy metal or based on mixtures of heavy metals.

The developer solution also preferably contains an antifogging agent to reduce the effects of fogging. It has been found that ethyl cysteine.HCl, or dimethyl cysteine dihydrochloride in combination with the dimethylamine borane yields excellent discrimination between image and background. Other antifoggants such as dimethylaminoethanethiol.HCl are also useful herein.

In the preferred embodiments of this invention, the physical development bath contains from 0.1% to 10% of the dimethylamine borane, from 0.1% to 10% of the transition metal salt or tetrazolium salt and from about 0.01% to 1% of the antifoggant.

The physical developer solution can contain additional materials such as complexing agents such as gluconic acid, tartaric acid, citric acid and ethylene diamine tetraacetic acid. It has been found that the use of gluconic acid produces superior results in sensitivity, stability and fog levels.

In addition, it is desirable to include SDS sensitizers in the physical developer solution. Thus, amounts of 0.1% to 1% of SDS in the developer solution results in greater sensitivity without excessive fogging. The development is generally carried out in 10 to 20 minutes.

Kits comprising the solution of palladium tetramine chloride and the physical developer solution are useful in treating the gel slabs. In this respect, it is preferred that the dimethylamine borane and the palladium complex be in different solutions in the visualization method.

The following examples are presented to illustrate more fully the invention.

EXAMPLE 1

A developer was prepared as follows:

| Solution A | |
|---|---|
| NiCl$_2$.6H$_2$O | 36 g |
| Sodium gluconate | 109 g |
| Dilute to 1 liter, adjust pH to 7.0 with concentrated NaOH. | |
| Solution B | |
| Dimethylamine borane (DMAB) | 3% (aq) |
| The two solutions were mixed as follows: | |
| Solution A | 40 ml |
| Solution B | 10 ml |
| Water | 55 ml |

A sensitizer Pd(NH$_3$)$_4$Cl$_2$ was prepared as follows: 3.6 g of PdCl$_2$ was mixed with 350 ml of deionized water and 50 ml of concentrated ammonium hydroxide. After stirring overnight, all of the PdCl$_2$ had dissolved. This solution was placed under aspirator vacuum for 8 hours and diluted to 500 ml with water to give a 1% solution of Pd(NH$_3$)$_4$Cl$_2$ whose final pH was 8.7.

Samples of β-Galactosidase at levels of 1, 0.1, and 0.01 μg/lane (0.75 mm slabs) were fixed in CH$_3$OH-H$_2$O (1:1) for at least one hour, and then developed as follows:

(1) rinsed in deionized water, 1 min.
(2) nucleated Pd(NH$_3$)$_4$Cl$_2$, 0.15%, 1 min.
(3) rinsed (deionized water) 1 min.
(4) developed 10–20 min.

The results were compared with those obtained by dye visualization. β-Galactosidase has two major electrophoretic bands. The minimum amount at 1 cm wide bands at which these bands can be observed using the dye stain visualization method (Stock Solutions 8, 9 and 10) where the procedure consisted of:
Solution 8: 2 hours
Solution 9: 1 hour
Solution 10: overnight
was approximately 1 μg. The minimum protein concentration that could be detected with the nickel development procedure was below 0.1 μg.

EXAMPLE 2

Effect of Antifoggant

A developer was prepared as described in Example 1 but with the addition of 10 μl of a 1% (methanol-water 1:1) solution of 1-phenyl-2-tetrazoline-5-thione commonly known as phenylmercaptotetrazole (PMT).

Samples of μ-Galactosidase in polyacrylamide gel (as described in Example 1) were developed as described in the four step sequence in Example 1. The minimum protein concentration that could be detected with this developer was less than 0.1 μg. The addition of the PMT caused a significant reduction in background fog. In addition, used developer solution which had often shown a propensity for spontaneous decomposition were now stable for an indefinite period of time.

EXAMPLE 3

Addition of SDS to Developer

A developer was prepared as in Example 2 but with the addition of sodium dodecyl sulfate (SDS) to give a SDS concentration in the developer of 0.44%.

Samples of μ-Galactosidase were nucleated as described in Example 1 and developed in the SDS containing developer. The fog was lower than that obtained in Example 2 where an antifoggant was used without the SDS addition, and the minimum protein concentration detected was less than 0.1 μg.

EXAMPLE 4

(comparative example)

Testing of Various Sensitizers

The following nucleating agents were used in place of the nucleating agent described in Example 1 (Pd(NH$_3$)$_4$Cl$_2$) with the same developer as described in Example 1. All were tested at the 0.1% level.
  A. Bis(ethylene diamine)palladium (II) chloride
  B. Chloro(N,N,N′,N′-tetraethyl diethylenetriamine)-palladium (II) hexafluorophosphate
  C. Potassium tetracyano palladate (II)
  D. Cupric Chloride The results for β-Galactosidase showed that minimum protein concentration of 1 to 0.1 βg could be detected but that much longer development times were required as compared with Pd(NH$_3$)$_4$Cl$_2$.

EXAMPLE 5

Variations of Complexing Agent

A developer was formulated as described in Example 1 but with the substitution of tartaric acid for gluconic acid. The results for β-Galactosidase were approximately the same as obtained in Example 1.

EXAMPLE 6

Variations in Proteins

A sample of human serum albumin was prepared following the procedure used for β-Galactosidase. A separation was carried out as described above for loading and running the gels and the electrophoregram developed using the composition described in Example 1. The minimum protein concentration that could be detected was less than 0.1 µg. Similar results were obtained with catalase.

EXAMPLE 7

Variations in Polyacrylamide Concentration

A separating gel was prepared using the formulation described above in preparing gel slabs except that the final acrylamide monomer concentration was twice (2%) that described above. A separation was carried out on human serum albumin and the slabs developed as described in Example 1. The results were the same as those described for slabs in which the polyacrylamide concentration was 10% (Example 5).

EXAMPLE 8

Variations in Slab Thickness

Electrophoretic separation of human serum albumin was carried out as described in Example 6 except that the slab thickness was 1.5 mm (instead of 0.75 mm). The development procedure described in Example 1 was carried out and the results (as compared with Example 6) were virtually identical.

EXAMPLE 9

Use of Sodium Dodecyl Sulfate in Nucleation Procedure

Samples of β-Galactosidase in polyacrylamide electrophoregrams (0.75 mm thick) containing 10% acrylamide and 2.7% methylene bisacrylamide were nucleated as follows:

| | | |
|---|---|---|
| 1. Water | | 1 min. |
| 2. Sodium Dodecyl Sulfate (2%) | | 1 min. |
| 3. Water | | 2 min. |
| 4. Pd(NH$_3$)$_4$Cl$_2$ (0.15%) | | 1 min. |
| 5. Water | | 1 min. |

This procedure caused the polyacrylamide slab to appear turbid. However, examination by transmitted light revealed the majority of the protein bands in the various lanes quite clearly. These appear as less turbid areas in contrast to the cloudy background. The sample was developed in the formulation described in Example 3. The protein concentrations were 1, 0.1, and 0.01 µg and after only 5 minutes development, the major bands at all three concentrations could be seen. After 30 minutes development, the rwo main bands and 3-4 additional bands could be detected at the 0.01 µg level.

EXAMPLE 10

Effect of Acid Fixing Treatment

A sample similar to that described in Example 9 was stored for two weeks in a solution of methanol-water (1:1) that also contained 10% (v/v) of acetic acid. This sample developed poorly (low density) after the sensitization and development procedures described in Example 9. However, soaking the electrophoregram in methanol-water (1:1) for 5 hours before sensitizing and developing gave a satisfactory visualization. The minimum protein concentration that could be detected was 0.01 µg.

EXAMPLE 11

Development of a Sample That Had Been Dye Stained

An electrophoregram of β-Galactosidase (2.5 µg) had been dye stained with Coomassie Brilliant Blue and stored in methanol-water (1:1). The sample was later removed from the storage solution and given the following sensitization and development procedure:

| | |
|---|---|
| 1. Water rinse | 20 min. |
| 2. Pd(NH$_3$)$_4$Cl$_2$ (0.15%) | 1 min. |
| 3. Water | 1 min. |
| 4. Development (as in Example 9) | 20 min. |

After the development step, the sample showed a good visulization pattern that was muck more dense than that of the dye stain, and several minor bands appeared that heretofore were not visible.

EXAMPLE 12

Visualization of Isoenzymes

Sample of isoenzymes (lactate dehydrogenase isotrol, Sigma Chemical Co.) which has 5 human lactate dehydrogenase isoenzymes was run in the standard 10% polyacrylamide (as described earlier) and run at concentrations of 100%, diluted 10 times and diluted 100 times. The dilutions were carried out with the tank buffer solution described above.

A sample was given the following nucleation and development procedure:

| | |
|---|---|
| 1. Water | 1 min. |
| 2. SDS 2% | 1 min. |
| 3. Water | 2 min. |
| 4. Pd(NH$_3$)$_4$Cl$_2$ (0.1%) | 1 min. |
| 5. Water | 5 min. |
| 6. Development (as in Example 9) | 10–30 min. |

The number of bands shown after 30 minutes development were compared with those that are visualized with the Coomassie Brilliant Blue Staining Procedure (for 0.01 x concentration).

| Coomassie Stain | Nickel Development |
|---|---|
| 1 faint band | 5 major bands and several minor bands |

Thus, the increase in sensitivity achieved by Nickel Development is at least 100 fold.

EXAMPLE 13

Use of a Dye-Forming Physical Developer

A developer was formulated as follows:

| | |
|---|---|
| 2,3,5-triphenyl-2H—tetrazolium chloride | 25 g |
| DMAB | 2.5 g |
| Water to one liter | |

Electrophoregrams of β-Galactosidase as described in Example 1 were nucleated with 0.15% Pd(NH$_3$)$_4$ Cl$_2$ for 1 minute, rinsed briefly with deionized water, and developed in the dye-forming physical developer for 10 minutes. The protein bands appeared as red images against a pink background. The minimum protein concentration detectable was approximately 0.1 µg.

EXAMPLE 14

Effect of Cationic Antifoggants

A developing solution was prepared as in Example 1, but with the addition of 10 μL of a 1% solution of ethyl cysteine.HCl.

An electrophoregram of β-Galactosidase in polyacrylamide gel was sensitized (as described in Example 9) and developed in the solution for 20 minutes at 25° C. After this time, the main protein band could be observed at protein concentrations as low as 1 ng. The fog level as measured with a transmittance densitometer was less than 0.7.

Substituting dimethylaminoethanethiol.HCl or dimethyl cysteine dihydrochloride (Aldrich) for the ethyl cysteine gave similar results.

EXAMPLE 15

Very Dilute Pd Sensitizing Solution

An electrophoregram of human serum albumin was nucleated by the procedure described in Example 9, except that the Pd solution was lowered to 0.01%. The immersion time in this sensitizing solution was increased from 1 minute to 10 minutes.

Development in the developer described in Example 14 gave the same sensitivity as was found at the higher Pd concentrations (0.1%) and shorter immersion times. However, the background in the dilute case was much higher (2.4) as compared with 1.0 for the short immersion time example.

EXAMPLE 16

Stabilizing of Developer Electrophoregrams

Following development, the electrophoregrams of Example 14 were washed in tap water for 15 minutes and stored under the following two sets of conditions:
(1) Water
(2) Sodium hypophosphite 10%

After a few days storage at room temperature, Sample #1 showed severe image loss whereas the sample stored in sodium hypophosphite was unchanged.

EXAMPLE 17

Non SDS Electrophoresis

A sample of human serum albumin was dissolved in the following solution to give a concentration of 1 μg protein per 1 μL solution.

| | |
|---|---|
| TRIS | 11.0 g |
| Boric Acid | 5.1 |
| EDTA (ethylene dinitrotetraacetic acid) | 0.95 |
| Sodium azide | 0.05 |

The above was dissolved in 1 liter of water and the final pH adjusted to 8.3 with NaOH. This solution was used as the buffer in the electrophoresis procedure.

A non SDS polyacrylamide gradient gel (sold by Separation Sciences) was used. This gel contains the solution described above. The albumin solution was placed in wells cut into the gel and electrophoresed for 5 hours at a constant voltage of 200 V. The gel was then removed and fixed in methanol and water (1:1) for 1 hour.

The gel was nucleated and developed as described in Examples 3 and 9.

After 20 minute development, protein bands at the 100 ng level could easily be detected. A control stained with Coomassie Blue gave a faint image at the 1000 ng level.

The invention has been described in detail with particular reference to preferred embodiments thereof, but it will be understood that variations and modifications can be effected within the spirit and scope of the invention.

What is claimed is:

1. A method for determining macromolecules in polyacrylamide gels, said method comprising the steps of
   (a) forming a latent stain image by nucleating the macromolecules in the gel with a palladium tetramine salt and
   (b) developing the latent stain image by treating the gel with a physical developer solution comprising dimethylamine borane and a member selected from the group consisting of a transition metal salt and a tetrazolium salt.
2. The method of claim 1 wherein the physical developer solution includes an antifoggant.
3. The method of claim 2 wherein the antifoggant is ethyl cysteine.HCl.
4. The method of claim 1 wherein the macromolecules in the gels have been subjected to electrophoresis prior to forming the stain.
5. The method of claim 1 wherein the macromolecules are proteins.
6. The method of claim 1 wherein the macromolecules are sensitized with sodium dodecyl sulfate prior to forming the gel.
7. The method of claim 1 wherein the physical developing solution includes a complexing agent.
8. The method of claim 7 wherein the complexing agent is gluconic acid or an ester thereof.
9. The method of claim 1 wherein the physical developing solution includes sodium dodecyl sulfate.
10. The method of claim 1 wherein the development is carried out for a period of 10 to 20 minutes.

* * * * *